United States Patent
Kawamura et al.

(10) Patent No.: US 11,486,388 B2
(45) Date of Patent: Nov. 1, 2022

(54) VALVE AND FLUID CONTROL APPARATUS

(71) Applicant: Murata Manufacturing Co., Ltd., Kyoto (JP)

(72) Inventors: Kenichiro Kawamura, Kyoto (JP); Tsuyoshi Waku, Kyoto (JP); Yukinori Sakuraya, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 151 days.

(21) Appl. No.: 17/136,587

(22) Filed: Dec. 29, 2020

(65) Prior Publication Data
US 2021/0115916 A1 Apr. 22, 2021

Related U.S. Application Data

(63) Continuation of application No. 15/844,718, filed on Dec. 18, 2017, now Pat. No. 10,883,494, which is a (Continued)

(30) Foreign Application Priority Data

May 24, 2013 (JP) .................................. 2013-109994

(51) Int. Cl.
*A61B 5/0235* (2006.01)
*F16K 99/00* (2006.01)
(Continued)

(52) U.S. Cl.
CPC .......... *F04B 53/1085* (2013.01); *A61B 5/022* (2013.01); *A61B 5/0235* (2013.01); (Continued)

(58) Field of Classification Search
CPC ............... A61B 5/0235; F16K 99/0015; F16K 2099/0073; F16K 2099/008; (Continued)

(56) References Cited

U.S. PATENT DOCUMENTS

| 4,852,851 A | 8/1989 | Webster |
| 6,033,191 A | 3/2000 | Kamper et al. |

(Continued)

FOREIGN PATENT DOCUMENTS

| EP | 2436961 A1 | 4/2012 |
| JP | 5-75558 U | 10/1993 |

(Continued)

OTHER PUBLICATIONS

International Search Report issued in Patent Application No. PCT/JP2014/062771 dated Aug. 12, 2014.
(Continued)

*Primary Examiner* — Paul J Gray
(74) *Attorney, Agent, or Firm* — Pearne & Gordon LLP

(57) ABSTRACT

A fluid control apparatus includes a piezoelectric pump and valve. The valve includes a second valve housing, second seal member, diaphragm, first seal member, and first valve housing and has a structure in which they are laminated in sequence. The first valve housing includes a second vent and third vent, has a valve seat, and includes six cavities. The second valve housing has a first vent and first vent and includes a valve seat and six first protrusions. The second valve housing further includes six second protrusions nearer the outer edges than the six first protrusions, as seen in the x-axis direction in plan view.

13 Claims, 13 Drawing Sheets

Related U.S. Application Data continuation of application No. 14/948,528, filed on Nov. 23, 2015, now Pat. No. 9,879,669, which is a continuation of application No. PCT/JP2014/062771, filed on May 14, 2014.

(51) Int. Cl.
| | | |
|---|---|---|
| *F04B 53/10* | (2006.01) | |
| *F16K 7/17* | (2006.01) | |
| *F16K 15/14* | (2006.01) | |
| *F16K 27/02* | (2006.01) | |
| *A61B 5/022* | (2006.01) | |
| *F16K 7/12* | (2006.01) | |

(52) U.S. Cl.
CPC .............. *F16K 7/12* (2013.01); *F16K 7/17* (2013.01); *F16K 15/144* (2013.01); *F16K 27/0236* (2013.01); *F04B 53/106* (2013.01); *F04B 53/1062* (2013.01); *F16K 99/0015* (2013.01); *F16K 2099/008* (2013.01); *F16K 2099/0073* (2013.01); *F16K 2099/0086* (2013.01)

(58) Field of Classification Search
CPC ...... F16K 2099/0086; F16K 7/12; F16K 7/17; F04B 53/106; F04B 53/1062
See application file for complete search history.

(56) References Cited

U.S. PATENT DOCUMENTS

| | | |
|---|---|---|
| 8,038,640 B2 | 10/2011 | Orr |
| 2004/0136843 A1 | 7/2004 | Jahn |
| 2009/0137940 A1 | 5/2009 | Orr |
| 2009/0242061 A1 | 10/2009 | Chen et al. |
| 2012/0244454 A1 | 9/2012 | Maeda |
| 2013/0178752 A1 | 7/2013 | Kodama |
| 2014/0030480 A1 | 1/2014 | Nitta |

FOREIGN PATENT DOCUMENTS

| | | |
|---|---|---|
| JP | 2007-046721 A | 2/2007 |
| WO | 89/05417 A1 | 6/1989 |
| WO | 2010/137578 A1 | 12/2010 |
| WO | 2012/141113 A1 | 10/2012 |
| WO | 2012/147477 A1 | 11/2012 |

OTHER PUBLICATIONS

Translation of Written Opinion issued in Patent Application No. PCT/JP2014/062771 dated Aug. 12, 2014.

VALVE AND FLUID CONTROL APPARATUS

CROSS REFERENCE TO RELATED APPLICATIONS

This is a Continuation of U.S. patent application Ser. No. 15/844,718 filed on Dec. 18, 2017, which is a Continuation of U.S. patent application Ser. No. 14/948,528 filed on Nov. 23, 2015, which is a Continuation of International Patent Application No. PCT/JP2014/062771 filed on May 14, 2014, which claims priority from Japanese Patent Application No. 2013-109994 filed on May 24, 2013. The contents of these applications are incorporated herein by reference in their entireties.

BACKGROUND

Technical Field

The present disclosure relates to a valve that prevents backflow of a fluid and to a fluid control apparatus that includes the valve.

Patent Document 1 discloses a fluid control apparatus including a valve.

The fluid control apparatus includes a piezoelectric pump and the valve. By joining the upper surface of the piezoelectric pump to the bottom surface of the valve, the valve is connected to the piezoelectric pump.

The valve has a cuff connection port that communicates with an arm band rubber tube of a cuff. By fitting the arm band rubber tube of the cuff into the cuff connection port in the valve, the fluid control apparatus is connected to the cuff.

The valve includes a second valve housing, a diaphragm made of a rectangular thin film, and a first valve housing and has a structure in which they are laminated in sequence.

Patent Document 1: International Publication No. 2012-141113

BRIEF SUMMARY

The valve described in Patent Document 1 may preferably have sufficient sealing between the second valve housing and the diaphragm and between the diaphragm and the first valve housing to prevent air from leaking from the inside of the valve.

After a study, the present inventor devised a valve having the structure described below.

FIG. 10 is a cross-sectional view of a main portion of a fluid control apparatus 900 according to a first comparative example. FIG. 11 is an exploded perspective view of a valve 901 illustrated in FIG. 10. FIG. 12 is a cross-sectional view of a main portion of the valve 901 illustrated in FIG. 10. In FIGS. 11 and 12, a z-axis direction, y-axis direction, and x-axis direction are illustrated.

The details of each component will be provided below. The z-axis direction indicates a direction in which members included in the valve 901 are laminated. The x-axis direction indicates a direction in which a check valve 160, a communication path 135, and an exhaust valve 170 are arranged. The y-axis direction indicates a direction perpendicular to the z-axis direction and the x-axis direction.

As illustrated in FIGS. 10 and 11, the valve 901 includes a second valve housing 192, a second seal member 952 made of a rectangular thin film, a diaphragm 920 made of a rectangular thin film, a first seal member 951 made of a rectangular thin film, and a first valve housing 191 and has a structure in which they are laminated in sequence.

As illustrated in FIGS. 10 and 11, the first valve housing 191 has a second vent 112 communicating with a cuff 109 and a third vent 113 communicating with the outside of a fluid control apparatus 900, includes a valve seat 139 protruding from the surrounding area of the third vent 113 toward the diaphragm 920, and has six cavities 182. The valve seat 139 has a cylindrical shape in which the third vent 113 is present in its central portion.

As illustrated in FIGS. 10 and 11, the bottom surface of the second valve housing 192 is bonded to the upper surface of a piezoelectric pump 10. As illustrated in FIGS. 10 and 11, the second valve housing 192 has a first vent 110 communicating with a discharge hole 56 in the piezoelectric pump 10 and a first vent 111 communicating with a discharge hole 55 in the piezoelectric pump 10, includes a columnar valve seat 138 protruding toward the diaphragm 920, and has six first protrusions 180 opposite the six cavities 182.

As illustrated in FIGS. 10 and 11, the diaphragm 920 has a circular hole portion 121 in the central portion in a region opposite the valve seat 138. The diameter of the hole portion 121 is smaller than that of a surface of the valve seat 138 that is in contact with the diaphragm 920.

The diaphragm 920 is held between the first valve housing 191 and the second valve housing 192 and is fixed to the first valve housing 191 and the second valve housing 192 such that it is in contact with the valve seat 139 and such that the surrounding area of the hole portion 121 is in contact with the valve seat 138. The valve seat 138 is disposed in the second valve housing 192 such that it presses the surrounding area of the hole portion 121 in the diaphragm 920.

Thus, the diaphragm 920 divides the inside of the first valve housing 191 and the second valve housing 192. The diaphragm 920 constitutes the check valve 160 including a ring-shaped first lower valve room 131 communicating with the first vent 111 and a columnar first upper valve room 133 communicating with the second vent 112 with the communication path 135 disposed therebetween, together with the first valve housing 191 and the second valve housing 192.

The diaphragm 920 also constitutes the exhaust valve 170 including a columnar second lower valve room 132 communicating with the first vent 110 and a ring-shaped second upper valve room 134 communicating with the first upper valve room 133 with the communication path 135 disposed therebetween, together with the first valve housing 191 and the second valve housing 192. The above-described shape of each of the valve rooms is a shape seen in a direction perpendicular to the diaphragm 920 in plan view. The check valve 160, communication path 135, and exhaust valve 170 are arranged along the x-axis direction.

The six cavities 182 in the first valve housing 191 are nearer the outer edges than the first lower valve room 131 and the second lower valve room 132, as seen in the x-axis direction in plan view. Of the six cavities 182, three cavities 182 are arranged along the x-axis direction. The other three cavities 182 are located on the opposite side to the previously described three cavities 182 such that the first lower valve room 131 and the second lower valve room 132 are disposed therebetween, and are arranged along the x-axis direction such that they are parallel with the previously described three cavities 182.

The six first protrusions 180 in the second valve housing 192 are nearer the outer edges than the first upper valve room 133 and the second upper valve room 134, as seen in the x-axis direction in plan view. The six first protrusions 180 are arranged opposite the six cavities 182.

The first seal member 951 has second through holes 156A to 156C in a region that faces the first upper valve room 133, communication path 135, and second upper valve room 134. The second through hole 156A may have a circular shape whose central axis is substantially coaxial with that of the first upper valve room 133, for example. The second through hole 156B may have a circular shape whose central axis is substantially coaxial with that of the second upper valve room 134, for example.

The second seal member 952 has first through holes 155A to 155B in a region that faces the first lower valve room 131 and second lower valve room 132. The first through hole 155A may have a circular shape whose central axis is substantially coaxial with that of the first lower valve room 131, for example. The first through hole 155B may have a circular shape whose central axis is substantially coaxial with that of the second lower valve room 132, for example.

Next, a method for manufacturing the valve 901 is described. First, the second valve housing 192, second seal member 952, diaphragm 920, first seal member 951, and first valve housing 191 are laminated, and the six first protrusions 180 are fit into the six cavities 182. In this way, the diaphragm 920 is held between the first valve housing 191 and the second valve housing 192 with the first seal member 951 and the second seal member 952 disposed therebetween.

Next, the multilayer body consisting of the second valve housing 192, second seal member 952, diaphragm 920, first seal member 951, and first valve housing 191 is placed on a stage S (see FIG. 12), and the end portions of the six first protrusions 180 are heat-staked. In this way, the end portions of the six first protrusions 180 are crushed, and the valve 901 is obtained.

The valve 901 described above needs further reducing its cost. In particular, it is necessary to use a highly reliable material in the diaphragm 920, and this leads to one factor of a high manufacturing cost of the valve 901.

The present inventor devised a valve 501 (see FIG. 13) including a first seal member 151, a second seal member 152, and a diaphragm 120, in which outer side portions J1 to J6 (see FIGS. 11 and 12) nearer the outer edges than the check valve 160 and the exhaust valve 170, as seen in the x-axis direction in plan view, and not directly contributing to the function as the valve are removed from the first seal member 951, diaphragm 920, and second seal member 952. The valve 501 has a reduced size of the area used by the diaphragm 920 and aims to reduce the manufacturing cost of the valve 901.

However, as illustrated in FIG. 13, in the inner side portion with respect to the first protrusions 180 in the valve 501, as seen in the x-axis direction, the first valve housing 191 and the second valve housing 192 hold the diaphragm 120 therebetween with the first seal member 151 and the second seal member 152 disposed therebetween. In contrast, in the outer side portion with respect to the first protrusions 180, the first valve housing 191 and the second valve housing 192 do not hold anything.

If the valve 501 is heat-staked as described above, the outer side portion with respect to the first protrusions 180 in the first valve housing 191 is warped toward the second valve housing 192, and the outer side portion with respect to the first protrusions 180 in the second valve housing 192 is warped toward the first valve housing 191.

Thus, the structure of the valve 501 has a problem in that leakage of air from the inside of the valve 501 is large and the performance of the valve 501 decreases.

As illustrated in FIG. 10, in the case of the fluid control apparatus 900, in which the valve 901 is connected to the piezoelectric pump 10, warpage of the valve 901 affects warpage of the piezoelectric pump 10. Therefore, there is also a problem in that this may lead to a decrease in the performance of the piezoelectric pump 10.

The present disclosure provides a valve capable of reducing its manufacturing cost without necessarily decreasing the performance of the valve, as compared with traditional valves and a fluid control apparatus including the valve.

The valve according to the present disclosure has a configuration described below to solve the above problems.

(1) The valve includes a diaphragm having a hole portion, a first seal member disposed on a first principal surface of the diaphragm, a first valve housing joined to the diaphragm with the first seal member disposed therebetween, the first valve housing having a first hole, a first valve room located near the first principal surface of the diaphragm and communicating with the first hole, and a plurality of cavities located in an outer side portion with respect to the first valve room, a second seal member disposed on a second principal surface of the diaphragm, and a second valve housing joined to the diaphragm with the second seal member disposed therebetween, the second valve housing having a second hole and a second valve room located near the second principal surface of the diaphragm and communicating with the second hole, the second valve housing including a plurality of first protrusions located in the outer side portion with respect to the second valve room.

The diaphragm is held between the first valve housing and the second valve housing with the first seal member and the second seal member disposed therebetween by fitting the plurality of first protrusions into the plurality of cavities, a surrounding area of the hole portion in the diaphragm is in contact with the second valve housing in the second valve room, and the hole portion is covered therewith, each of the first seal member, the diaphragm, and the second seal member has a circumference smaller than a circumference of each of the first valve housing and the second valve housing and is disposed in an inner side portion with respect to the plurality of first protrusions, and at least one of the first valve housing and the second valve housing includes a plurality of second protrusions located in the outer side portion with respect to the plurality of first protrusions.

The valve of this configuration has the structure in which the first valve housing, first seal member, diaphragm, second seal member, and second valve housing are laminated. In this configuration, the circumference of the diaphragm is smaller than that of each of the first valve housing and the second valve housing and is disposed in the inner side portion with respect to the plurality of first protrusions. Thus, this configuration can have a smaller size of the area used by the diaphragm, as compared with the valve 901 (see FIG. 11) according to the first comparative example, which has the structure in which the circumference of the diaphragm is the same as that of each of the first valve housing and the second valve housing.

In the valve of this configuration, in the inner side portion with respect to the first protrusions, as seen in the x-axis direction in plan view, the first valve housing and the second valve housing hold the diaphragm therebetween with the first seal member and the second seal member disposed therebetween. In contrast, in the outer side portion with respect to the first protrusions, as seen in the x-axis direction in plan view, the plurality of second protrusions are located between the first valve housing and the second valve housing.

Thus, when the multilayer body consisting of the first valve housing, first seal member, diaphragm, second seal member, and second valve housing is placed on the stage and the end portions of the plurality of first protrusions are heat-stacked, the plurality of second protrusions come into contact with the first valve housing or second valve housing, and warpage of the outer side portion with respect to the first protrusions in the first valve housing and second valve housing can be suppressed. That is, this configuration can suppress leakage of air from the inside of the valve.

Consequently, according to this configuration, the manufacturing cost of the valve can be reduced without necessarily decreasing the performance of the valve, as compared with traditional valves.

(2) Each of the plurality of second protrusions may have a height smaller than a height of each of the plurality of first protrusions.

In this configuration, the end portions of the plurality of first protrusions, which protrude toward the second valve housing further than the plurality of second protrusions, are heat-staked.

(3) The height of each of the plurality of second protrusions may be equal to a sum of a thickness of the first seal member and a thickness of the second seal member.

In this configuration, the plurality of second protrusions, each having the same height as the sum of the thickness of the first seal member and that of the second seal member, are located between the outer side portion with respect to the first protrusions in the first valve housing and the outer side portion with respect to the first protrusions in the second valve housing.

Thus, when the end portions of the plurality of first protrusions are heat-staked as described above, because the plurality of second protrusions come into contact with the first valve housing or second valve housing, warpage of the outer side portions with respect to the first protrusions in the first valve housing and in the second valve housing can be further suppressed. That is, this configuration can further suppress leakage of air from the inside of the valve.

Consequently, according to this configuration, the manufacturing cost of the valve can be reduced without necessarily decreasing the performance of the valve, as compared with traditional valves.

The fluid control apparatus according to the present disclosure has a configuration described below to solve the above problems.

(4) The fluid control apparatus includes a pump having a discharge hole, and the valve according to any one of the above-described (1) to (3).

The first hole in the first valve housing is connected to a fluid storage portion that stores fluid, and the second hole in the second valve housing is connected to the discharge hole in the pump.

By using the valve in any one of the above-described (1) to (3), the fluid control apparatus including that valve can achieve substantially the same advantages.

According to the present disclosure, the manufacturing cost of the valve can be reduced without necessarily decreasing the performance of the valve, as compared with traditional valves.

DESCRIPTION OF EMBODIMENTS

A fluid control apparatus 100 according to an embodiment of the present disclosure is described below.

Figure 1:
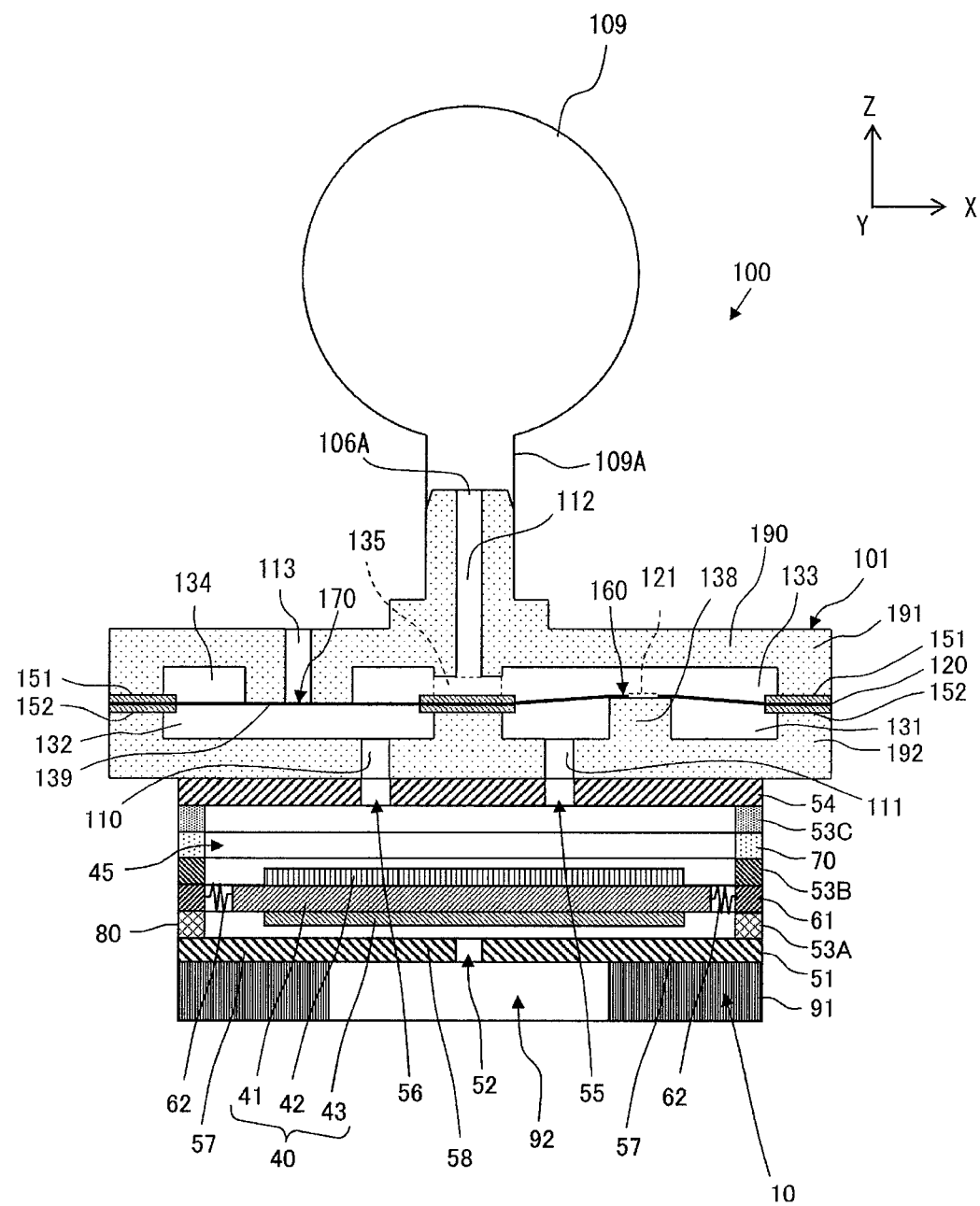
FIG. 1 is a cross-sectional view of a main portion of a fluid control apparatus 100 according to an embodiment of the present disclosure.

FIG. 1 is a cross-sectional view of a main portion of the fluid control apparatus 100 according to the embodiment of the present disclosure. The fluid control apparatus 100 includes a piezoelectric pump 10 and a valve 101. The fluid control apparatus 100 is an apparatus for measuring blood pressure of a subject. By joining the upper surface of the piezoelectric pump 10 to the bottom surface of the valve 101, the valve 101 is connected to the piezoelectric pump 10.

The valve 101 has a cuff connection port 106A communicating with an arm band rubber tube 109A of a cuff 109. By fitting the arm band rubber tube 109A of the cuff 109 into the cuff connection port 106A in the valve 101, the fluid control apparatus 100 is connected to the cuff 109.

The cuff 109 corresponds to "fluid storage portion" in the present disclosure.

The structure of each of the piezoelectric pump 10 and the valve 101 is described. First, the structure of the piezoelectric pump 10 is described with reference to FIGS. 1 and 2.

Figure 2:
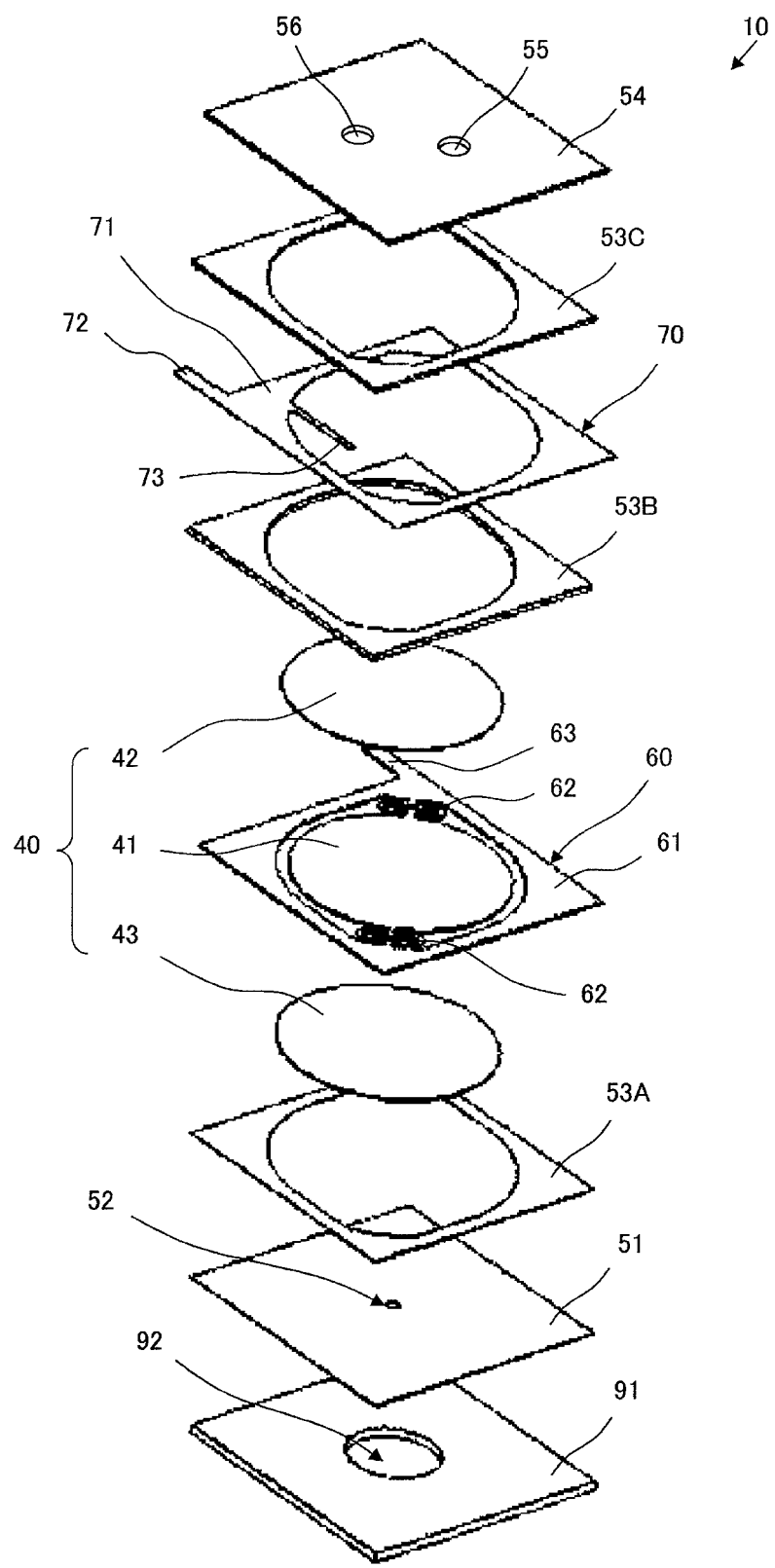
FIG. 2 is an exploded perspective view of a piezoelectric pump 10 illustrated in FIG. 1.

FIG. 2 is an exploded perspective view of the piezoelectric pump 10 illustrated in FIG. 1. The piezoelectric pump 10 includes a base 91, a flexible plate 51, a spacer 53A, a strengthening plate 43, a vibrating plate unit 60, a piezoelectric element 42, a spacer 53B, an electrode conduction plate 70, a spacer 53C, and a lid plate 54 and has a structure in which they are laminated in sequence.

The base 91, flexible plate 51, spacer 53A, part of the vibrating plate unit 60, spacer 53B, electrode conduction plate 70, spacer 53C, and lid plate 54 constitute a pump housing 80. The inner space of the pump housing 80 corresponds to a pump room 45.

The vibrating plate unit 60 includes a vibrating plate 41, a frame plate 61, coupling portions 62, and an external terminal 63. The vibrating plate unit 60 is formed by punching on a metal plate.

The frame plate 61 is disposed on the periphery of the vibrating plate 41. The external terminal 63 for electric connection is disposed on the frame plate 61. The vibrating plate 41 is coupled to the frame plate 61 by the coupling portions 62. The coupling portions 62 may have a thin ring shape. The coupling portions 62 have an elastic structure having elasticity of a small spring constant.

Accordingly, the vibrating plate 41 is elastically supported on the frame plate 61 at two points with flexibility by the two coupling portions 62. Thus, bending vibration of the vibrating plate 41 is not substantially hindered. That is, the peripheral portion (of course, central portion) of a piezoelectric actuator 40 is not virtually restrained.

In the example illustrated in FIG. 2, the coupling portions 62 are disposed at two points. The coupling portions 62 may also be disposed at three points. The coupling portions 62 do not interfere with vibration of the piezoelectric actuator 40, but have an effect on vibration of the piezoelectric actuator 40 to some degree. Thus, if the three coupling portions 62 are used, for example, the vibrating plate 41 can be supported more naturally and cracking of the piezoelectric element 42 can also be prevented.

The piezoelectric element 42 is disposed on the upper surface of the disc-shaped vibrating plate 41. The strengthening plate 43 is disposed on the lower surface of the vibrating plate 41. The vibrating plate 41, piezoelectric element 42, and strengthening plate 43 constitute the disc-shaped piezoelectric actuator 40. The piezoelectric element 42 may be made of a PZT-based ceramic material, for example.

The vibrating plate 41 may also be made of a metal plate having a coefficient of linear expansion larger than that of each of the piezoelectric element 42 and the strengthening plate 43, and it may be thermoset at the time of bonding. This can avoid warpage of the whole piezoelectric actuator 40, enable appropriate compressive stress to remain in the piezoelectric element 42, and prevent cracking of the piezoelectric element 42.

For example, the vibrating plate 41 may be made of a material having a large coefficient of linear expansion, such as phosphor bronze (C5210) or stainless steel SUS301, and the strengthening plate 43 may be made of 42 nickel, 36 nickel, or stainless steel SUS430.

For the vibrating plate 41, piezoelectric element 42, and strengthening plate 43, the arrangement in which the piezoelectric element 42, strengthening plate 43, and vibrating plate 41 are positioned in this order from above may also be used. In this case, the coefficient of linear expansion is also adjusted by setting the materials of the strengthening plate 43 and vibrating plate 41 to enable appropriate compressive stress to remain in the piezoelectric element 42.

The spacer 53B is disposed on the upper surface of the frame plate 61. The spacer 53B is made of resin. The thickness of the spacer 53B is the same as or slightly larger than that of the piezoelectric element 42. The frame plate 61 electrically insulates the electrode conduction plate 70 and the vibrating plate unit 60.

The electrode conduction plate 70 is disposed on the upper surface of the spacer 53B. The electrode conduction plate 70 is made of metal. The electrode conduction plate 70 includes a frame member 71 that opens substantially circularly, an internal terminal 73 protruding into this opened space, and an external terminal 72 protruding toward the outside.

The end of the internal terminal 73 is joined to the surface of the piezoelectric element 42 by soldering. By setting the location of the soldered joint as the location corresponding to a node of bending vibration of the piezoelectric actuator 40, vibration of the internal terminal 73 is suppressed.

The spacer 53C is disposed on the upper surface of the electrode conduction plate 70. The spacer 53C is made of resin. The spacer 53C has a thickness similar to that of the piezoelectric element 42. The spacer 53C is a spacer for preventing the solder portion in the internal terminal 73 from coming into contact with the lid plate 54 when the piezoelectric actuator 40 vibrates. The spacer 53C also prevents a decrease in vibration amplitude caused by air resistance produced by the surface of the piezoelectric element 42 excessively getting close to the lid plate 54. Thus, the thickness of the spacer 53C may be similar to that of the piezoelectric element 42.

The lid plate 54 is disposed on the upper surface of the spacer 53C. The lid plate 54 has discharge holes 55 and 56. The lid plate 54 covers the upper portion of the piezoelectric actuator 40.

The spacer 53A is disposed on the lower surface of the vibrating plate unit 60. That is, the spacer 53A is disposed between the upper surface of the flexible plate 51 and the lower surface of the vibrating plate unit 60. The spacer 53A has a thickness in which approximately several tens of micrometers is added to the thickness of the strengthening plate 43. The spacer 53A is a spacer for preventing the piezoelectric actuator 40 from coming into contact with the flexible plate 51 when the piezoelectric actuator 40 vibrates.

The flexible plate 51 is disposed on the lower surface of the spacer 53A. The flexible plate 51 has a suction hole 52 in its center.

The base 91 is disposed on the lower surface of the flexible plate 51. The base 91 has a columnar cavity 92 in its central portion. The flexible plate 51 includes a fixed portion 57 fixed to the base 91 and a movable portion 58 nearer the center than the fixed portion 57 and facing the cavity 92.

The movable portion 58 can vibrate at substantially the same frequency as that for the piezoelectric actuator 40 due to pressure changes in air produced by vibration of the piezoelectric actuator 40. The natural frequency of the movable portion 58 is designed to be the same as or slightly lower than the driving frequency of the piezoelectric actuator 40.

When the vibration of the flexible plate 51 is designed to have a phase that lags the phase of vibration of the piezoelectric actuator 40 (for example, with a lag of 90 degrees), changes in thickness of the gap between the flexible plate 51 and the piezoelectric actuator 40 substantially increase.

Accordingly, when an alternating driving voltage is applied to the external terminals 63 and 72, the piezoelectric actuator 40 bends and vibrates concentrically. In addition, the movable portion 58 in the flexible plate 51 also vibrates together with the vibration of the piezoelectric actuator 40. In this way, the piezoelectric pump 10 sucks air into the pump room 45 through the cavity 92 and the suction hole 52. Additionally, the piezoelectric pump 10 discharges air from the pump room 45 through the discharge holes 55 and 56.

At this time, the peripheral portion of the piezoelectric actuator 40 in the piezoelectric pump 10 is not substantially fixed. Thus, according to the piezoelectric pump 10, the loss involving with vibration of the piezoelectric actuator 40 is small, and a high discharge pressure and a large discharge flow quantity are obtainable while the piezoelectric pump 10 keeps its small size and low profile.

Next, the structure of the valve 101 is described with reference to FIGS. 1 and 3 to 6.

Figure 3:
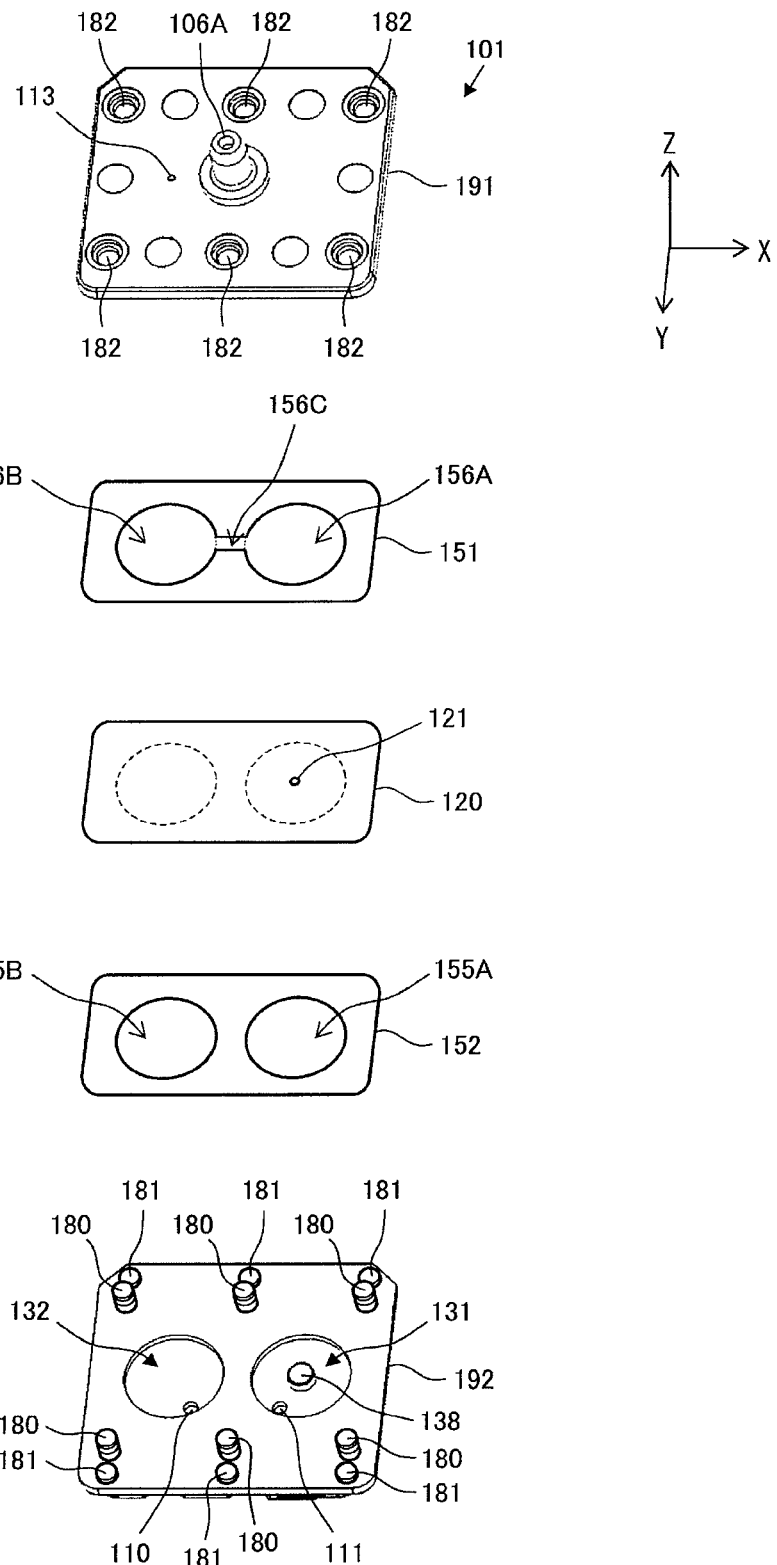
FIG. 3 is an exploded perspective view of a valve 101 illustrated in FIG. 1.
Figure 4:
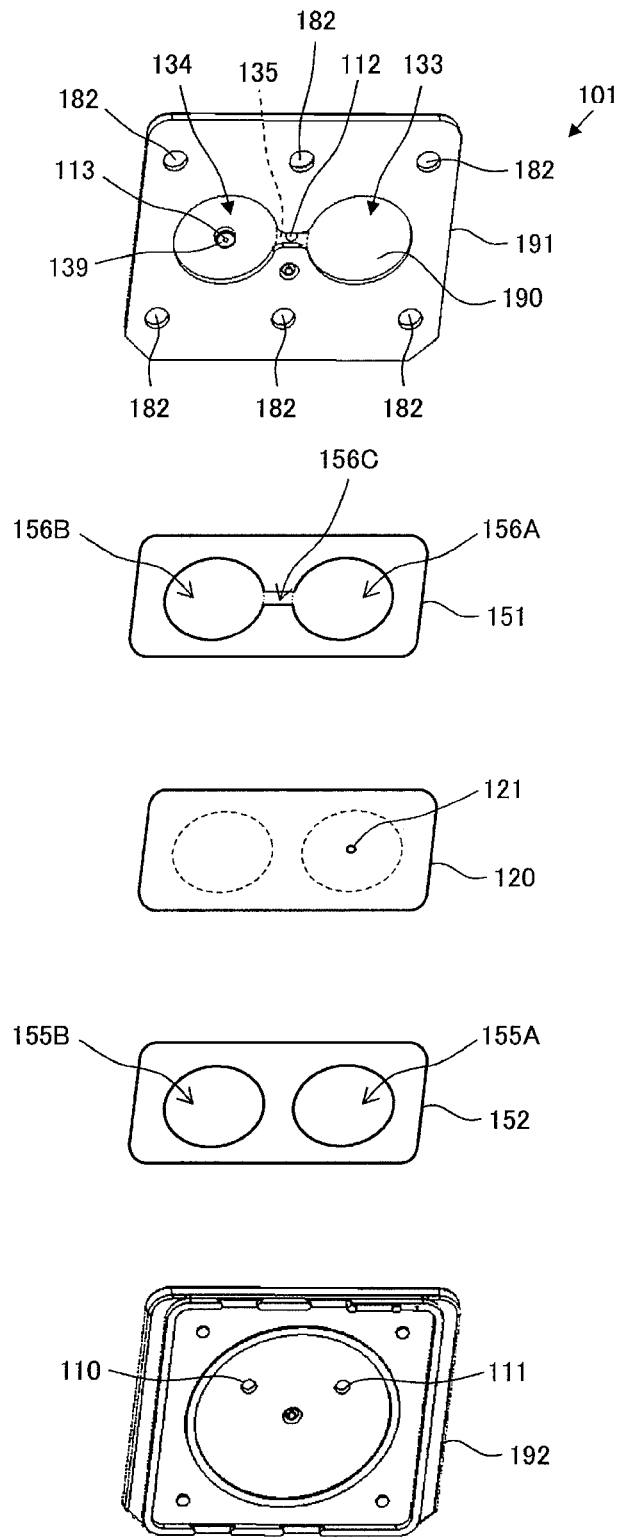
FIG. 4 is an exploded perspective view of the valve 101 illustrated in FIG. 1.
Figure 5:
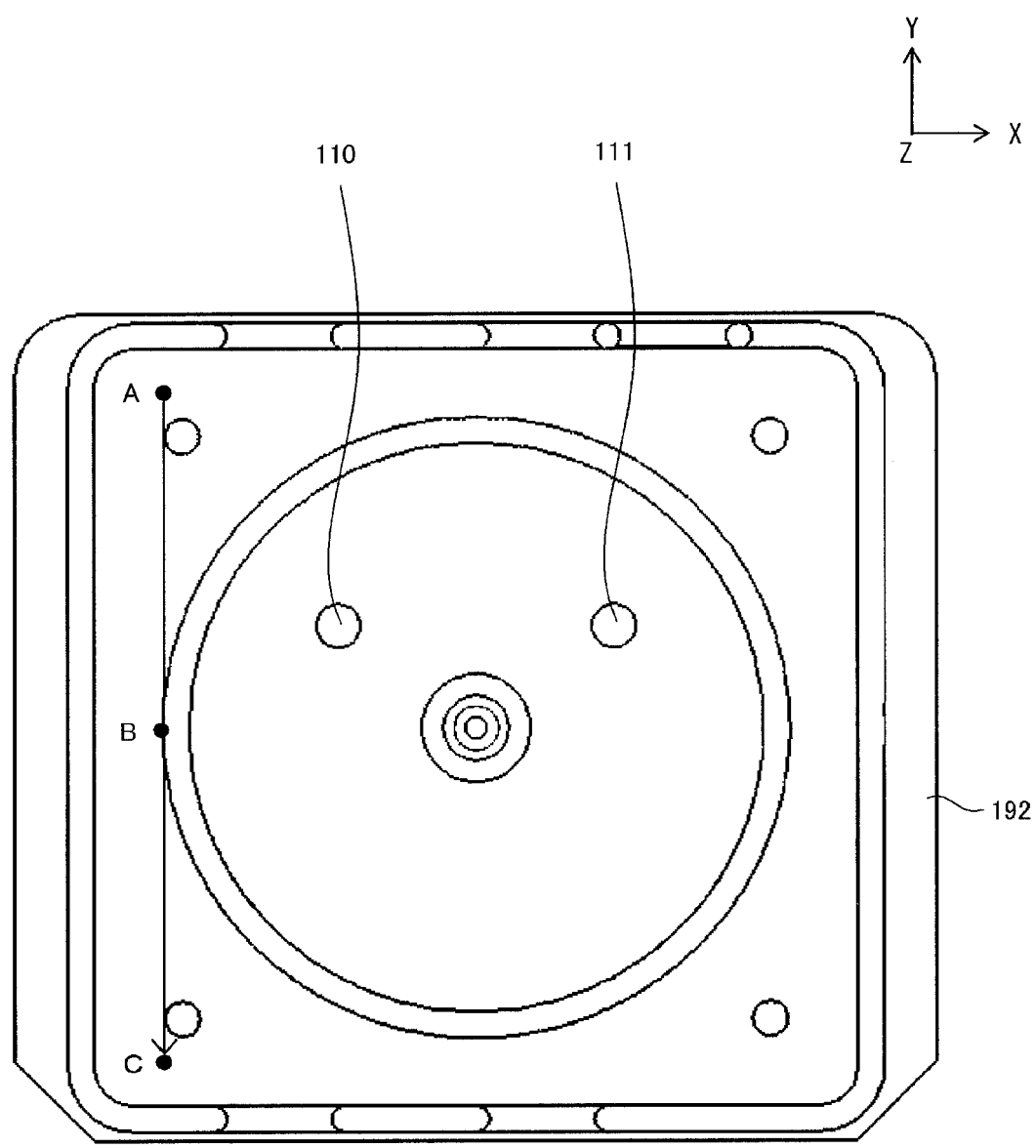
FIG. 5 is a bottom view of a second valve housing 192 included in the valve 101 illustrated in FIG. 1.
Figure 6:
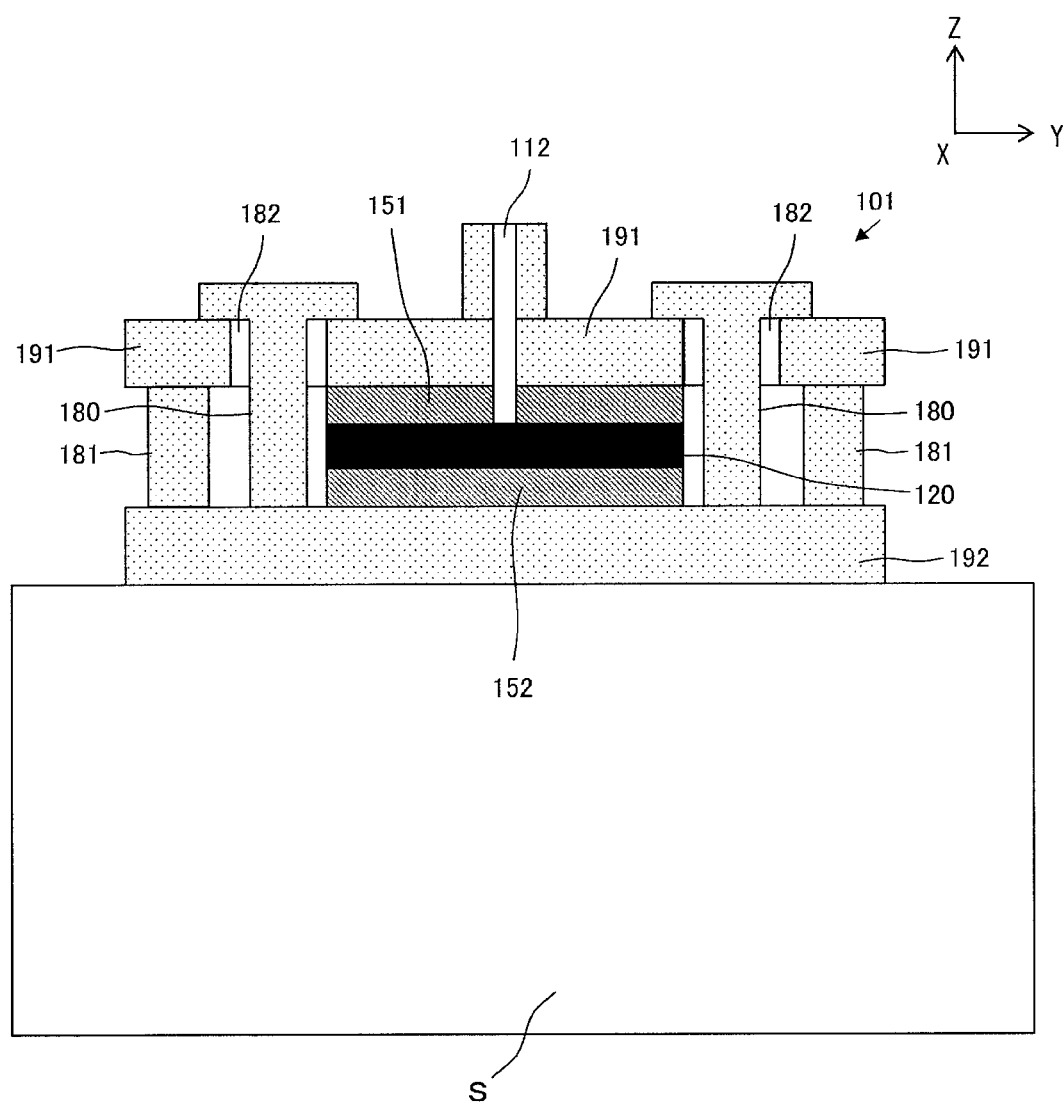
FIG. 6 is a cross-sectional view of a main portion of the valve 101 illustrated in FIG. 1.

FIGS. 3 and 4 are exploded perspective views of the valve 101 illustrated in FIG. 1. FIG. 3 is an exploded perspective view of the valve 101 seen from the upper surface side where it is connected to the cuff 109. FIG. 4 is an exploded perspective view of the valve 101 seen from the bottom surface side where it is joined to the piezoelectric pump 10. FIG. 5 is a bottom view of a second valve housing 192 included in the valve 101 illustrated in FIG. 1. FIG. 6 is a cross-sectional view of a main portion of the valve 101 illustrated in FIG. 1.

In FIGS. 3, 5, and 6, a z-axis direction, y-axis direction, and x-axis direction are illustrated. The z-axis direction indicates a direction in which the members included in the valve 101 are laminated. The x-axis direction indicates a direction in which a check valve 160, a communication path 135, and an exhaust valve 170 are arranged. The y-axis direction indicates a direction perpendicular to the z-axis direction and x-axis direction.

A "first hole" in the present disclosure corresponds to a second vent 112. A "second hole" in the present disclosure corresponds to first vents 110 and 111. A "first valve room" in the present disclosure corresponds to a first upper valve room 133 and a second upper valve room 134. A "second valve room" in the present disclosure corresponds to a first lower valve room 131 and a second lower valve room 132.

As illustrated in FIGS. 1, 3, 4, and 5, the valve 101 includes a second valve housing 192, a second seal member 152 made of a rectangular thin film, a diaphragm 120 made of a rectangular thin film, a first seal member 151 made of a rectangular thin film, and a first valve housing 191 and has a structure in which they are laminated in sequence.

As illustrated in FIGS. 1, 3, and 4, the first valve housing 191 has a second vent 112 communicating with the cuff 109, a third vent 113 communicating with the outside of the fluid control apparatus 100, includes a valve seat 139 protruding from the surrounding area of the third vent 113 toward the diaphragm 120, and has six cavities 182. The first valve housing 191 may be made of resin, for example. The valve seat 139 has a cylindrical shape having the third vent 113 in its central portion.

The six cavities 182 in the first valve housing 191 are nearer the outer edges than the first lower valve room 131 and the second lower valve room 132, which are described below, as seen in the x-axis direction in plan view. Of the six cavities 182, three cavities 182 are arranged along the x-axis direction. The other three cavities 182 are located on the opposite side to the previously described three cavities 182 such that the first lower valve room 131 and the second lower valve room 132 are disposed therebetween, and are arranged along the x-axis direction such that they are parallel with the previously described three cavities 182.

As illustrated in FIG. 1, the bottom surface of the second valve housing 192 is bonded to the upper surface of the piezoelectric pump 10. As illustrated in FIGS. 1, 3, 4, and 5, the second valve housing 192 has the first vent 110 communicating with the discharge hole 56 in the piezoelectric pump 10, the first vent 111 communicating with the discharge hole 55 in the piezoelectric pump 10, includes a columnar valve seat 138 protruding toward the diaphragm 120, and has six first protrusions 180 opposite the six cavities 182. The second valve housing 192 may be made of resin, for example. The six first protrusions 180 in the second valve housing 192 are nearer the outer edges than the first upper valve room 133 and the second upper valve room 134, which are described below, as seen in the x-axis direction in plan view.

The second valve housing 192 further includes six second protrusions 181 nearer the outer edges than the six first protrusions 180, as seen in the x-axis direction in plan view.

In the state where the six first protrusions 180 are fit in the six cavities 182, the six second protrusions 181 are nearer the outer edges than the first seal member 151, diaphragm 120, and second seal member 152, as seen in the x-axis direction in plan view.

As illustrated in FIGS. 1, 3, and 4, the diaphragm 120 has a circular hole portion 121 in the central portion in a region opposite the valve seat 138. The diameter of the hole portion 121 is smaller than that of a surface of the valve seat 138 that is in contact with the diaphragm 120. The circumference of the diaphragm 120 is smaller than that of each of the first valve housing 191 and the second valve housing 192. The diaphragm 120 may be made of rubber, such as ethylene propylene diene rubber (EPDM) or silicone, for example.

By fitting the six first protrusions 180 into the six cavities 182, the diaphragm 120 is held between the first valve housing 191 and the second valve housing 192 with the first seal member 151 and second seal member 152 disposed therebetween.

Thus, as illustrated in FIG. 6, the diaphragm 120 covers the inner side region in the first valve housing 191 with respect to the six cavities 182, as seen in the x-axis direction in plan view, and the inner side region in the second valve housing 192 with respect to the six first protrusions 180, as seen in the x-axis direction in plan view, and is in contact with the valve seat 138, and the surrounding area of the hole portion 121 is in contact with the valve seat 138. The valve seat 138 is disposed in the second valve housing 192 such that it presses the surrounding area of the hole portion 121 in the diaphragm 120.

The diaphragm 120 divides the inside of the first valve housing 191 and the second valve housing 192. The diaphragm 120 constitutes the check valve 160 including the ring-shaped first lower valve room 131 communicating with the first vent 111 and the columnar first upper valve room 133 communicating with the second vent 112 with the communication path 135 disposed therebetween, together with the first valve housing 191 and the second valve housing 192.

The diaphragm 120 also constitutes the exhaust valve 170 including the columnar second lower valve room 132 communicating with the first vent 110 and the ring-shaped second upper valve room 134 communicating with the first upper valve room 133 with the communication path 135 disposed therebetween, together with the first valve housing 191 and the second valve housing 192.

The above-described shape of each of the valve rooms is a shape seen in a direction perpendicular to the diaphragm 120 in plan view. The check valve 160, communication path 135, and exhaust valve 170 are arranged along the x-axis direction.

One example of the diameter of each of the first lower valve room 131, second lower valve room 132, first upper valve room 133, and second upper valve room 134 may be 7.0 mm. One example of the diameter of the surface of the valve seat 138 in contact with the diaphragm 120 may be 1.5 mm.

The first seal member 151 has second through holes 156A to 156C in a region that faces the first upper valve room 133, communication path 135, and second upper valve room 134. The second through hole 156A may have a circular shape whose central axis is substantially coaxial with that of the first upper valve room 133, for example. The second through hole 156B may have a circular shape whose central axis is substantially coaxial with that of the second upper valve room 134, for example.

One example of the diameter of each of the second through holes 156A and 156B may be 6.6 mm. That is, the circumference of the first seal member 151 is smaller than that of each of the first valve housing 191 and the second valve housing 192. The first seal member 151 may be made of double-sided tape or adhesive, for example.

The second seal member 152 has first through holes 155A and 155B in a region that faces the first lower valve room 131 and second lower valve room 132. The first through hole 155A may have a circular shape whose central axis is substantially coaxial with that of the first lower valve room 131, for example. The first through hole 155B may have a circular shape whose central axis is substantially coaxial with that of the second lower valve room 132, for example.

One example of the diameter of each of the first through holes 155A and 155B may be 6.6 mm. That is, the circumference of the second seal member 152 is smaller than that of each of the first valve housing 191 and the second valve housing 192. The second seal member 152 may be made of double-sided tape or adhesive, for example.

The diameter of the first through hole 155A is larger than that of the valve seat 138 and smaller than that of the first lower valve room 131. That is, the circumference of the first through hole 155A is larger than that of the valve seat 138 and smaller than that of the first lower valve room 131. Similarly, the diameter of the first through hole 155B is smaller than that of the second lower valve room 132. That is, the circumference of the first through hole 155B is smaller than that of the second lower valve room 132.

As described above, part of the first seal member 151 is located inside the first upper valve room 133 and the second upper valve room 134 in the valve 101. Similarly, part of the second seal member 152 is located inside the first lower valve room 131 and the second lower valve room 132. As illustrated in FIG. 1, the valve 101 includes the check valve 160 and the exhaust valve 170.

First, the check valve 160 includes part of the second valve housing 192 that has the first vent 111, part of the first valve housing 191 that has the second vent 112, the surrounding area of the hole portion 121 in the diaphragm 120, and the valve seat 138 being in contact with that surrounding area and covering the hole portion 121. The check valve 160 allows fluid to flow from the first lower valve room 131 toward the first upper valve room 133 and blocks fluid from flowing from the first upper valve room 133 toward the first lower valve room 131.

In the check valve 160, the diaphragm 120 comes into contact with or becomes separated from the valve seat 138 in accordance with a difference between the pressure in the first lower valve room 131 and that in the first upper valve room 133.

Next, the exhaust valve 170 includes part of the second valve housing 192 that has the first vent 110, part of the first valve housing 191 that has the second vent 112 and the third vent 113, part of the diaphragm 120, and the valve seat 139 protruding from the surrounding area of the third vent 113 toward the diaphragm 120, being in contact with the diaphragm 120, and being covered therewith.

In the exhaust valve 170, the diaphragm 120 comes into contact with or becomes separated from the valve seat 139 in accordance with a difference between the pressure in the second lower valve room 132 and that in the second upper valve room 134.

Next, a method for manufacturing the valve 101 is described. First, the second valve housing 192, second seal member 152, diaphragm 120, first seal member 151, and first valve housing 191 are laminated, and the six first protrusions 180 are fit into the six cavities 182. In this way, the diaphragm 120 is held between the first valve housing 191 and the second valve housing 192 with the first seal member 151 and the second seal member 152 disposed therebetween.

Next, the multilayer body consisting of the second valve housing 192, second seal member 152, diaphragm 120, first seal member 151, and first valve housing 191 is placed on a stage S (see FIG. 6), and the end portions of the six first protrusions 180 are heat-staked. In this way, the end portions of the six first protrusions 180 are crushed, and the valve 101 illustrated in FIG. 6 is obtained.

As illustrated in FIG. 6, in the inner side portion with respect to the first protrusions 180 in the valve 101, as seen in the x-axis direction in plan view, the first valve housing 191 and the second valve housing 192 hold the diaphragm 120 with the first seal member 151 and the second seal member 152 disposed therebetween. In contrast, in the outer side portion with respect to the first protrusions 180, the six second protrusions 181 are disposed.

Thus, when the multilayer body consisting of the first valve housing 191, first seal member 151, diaphragm 120, second seal member 152, and second valve housing 192 is placed on the stage S and the end portions of the six first protrusions 180 are heat-staked, because the outer side portion with respect to the first protrusions 180 in the first valve housing 191 is in contact with the six second protrusions 181, warpage of the outer side portion with respect to the first protrusions 180 in the first valve housing 191 toward the second valve housing 192 can be suppressed and warpage of the outer side portion with respect to the first protrusions 180 in the second valve housing 192 toward the first valve housing 191 can be suppressed. That is, in the present embodiment, leakage of air from the inside of the valve 101 can be suppressed.

Consequently, according to the present embodiment, the manufacturing cost of the valve 101 can be reduced without necessarily decreasing the performance of the valve, as compared with traditional valves.

The height of each of the six second protrusions 181 may be equal to the sum of the thickness of the first seal member 151, that of the diaphragm 120, and that of the second seal member 152. In this case, the six second protrusions 181, each having the same height as the sum of the thickness of the first seal member 151, that of the diaphragm 120, and that of the second seal member 152, are located between the outer side portion with respect to the first protrusions 180 in the first valve housing 191 and the outer side portion with respect to the first protrusions 180 in the second valve housing 192.

Thus, when the end portions of the six first protrusions 180 are heat-staked as described above, because the outer side portion with respect to the first protrusions 180 in the first valve housing 191 is in contact with the six second protrusions 181, warpage of the outer side portions with respect to the first protrusions 180 in the first valve housing 191 and in the second valve housing 192 can be further suppressed. That is, leakage of air from the inside of the valve 101 can be further suppressed.

Next, operations of the fluid control apparatus 100 during blood pressure measurement are described.

Figure 7:
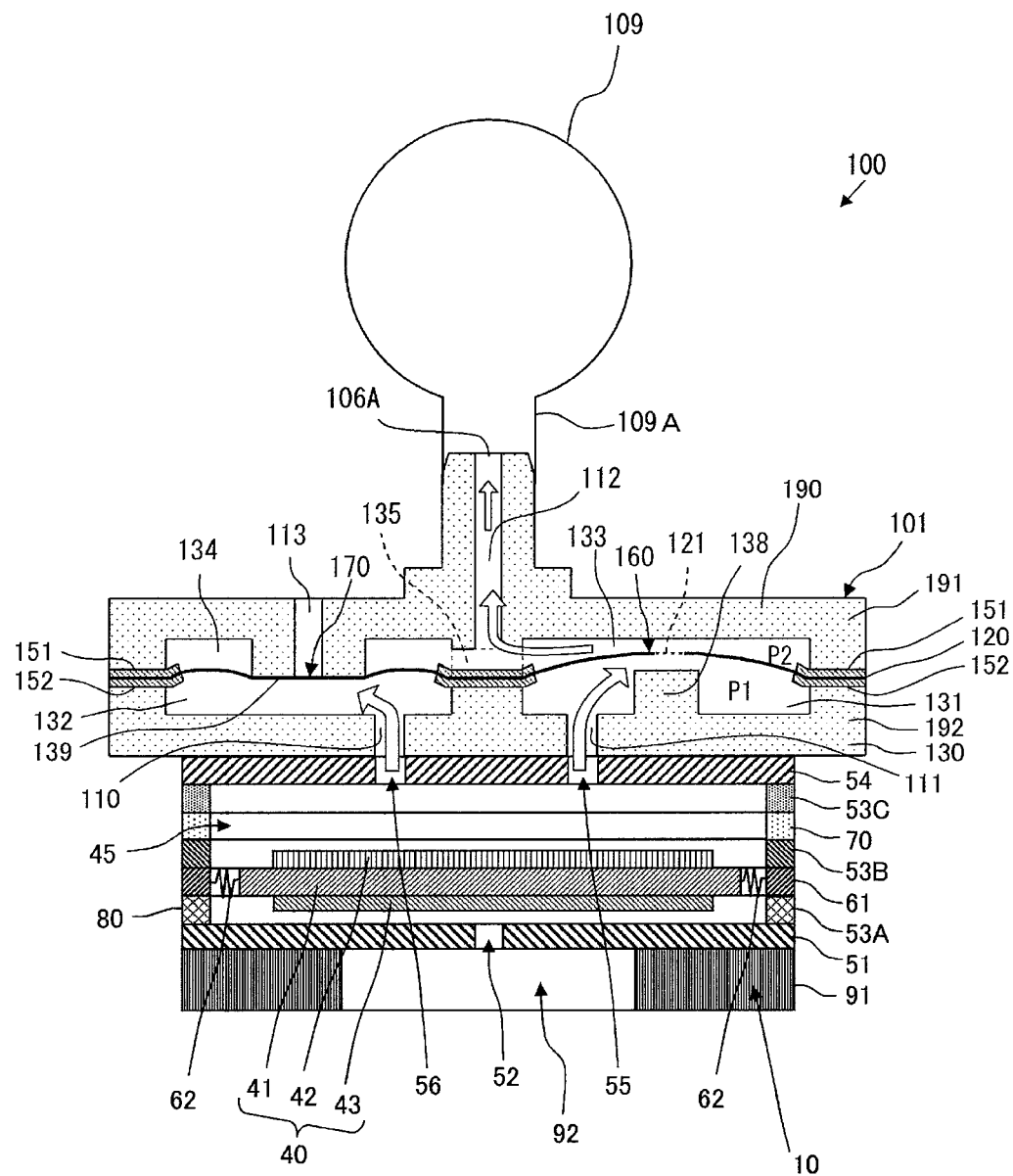
FIG. 7 is an illustration for describing air streams in the fluid control apparatus 100 while the piezoelectric pump 10 illustrated in FIG. 1 is driven.

FIG. 7 is an illustration for describing air streams in the fluid control apparatus 100 while the piezoelectric pump 10 illustrated in FIG. 1 is driven.

To start measuring a blood pressure, the fluid control apparatus 100 first drives the piezoelectric pump 10. When the piezoelectric pump 10 is driven, air is first sucked into the pump room 45 in the piezoelectric pump 10 through the cavity 92 and the suction hole 52. Then, the air is discharged through the ports 55 and 56 and flows into both the second lower valve room 132 and the first lower valve room 131 in the valve 101.

In this way, in the exhaust valve 170, the pressure in the second lower valve room 132 is higher than that in the second upper valve room 134. Thus, as illustrated in FIG. 7, the diaphragm 120 seals the third vent 113 and blocks passage of air between the second vent 112 and the third vent 113.

In the check valve 160, the pressure in the first lower valve room 131 is higher than that in the first upper valve room 133. Thus, the surrounding area of the hole portion 121 in the diaphragm 120 becomes separated from the valve seat 138, and the first vent 111 and the second vent 112 communicate with each other through the hole portion 121.

Therefore, air is sent from the piezoelectric pump 10 to the cuff 109 through the first vent 111, hole portion 121, and second vent 112 in the valve 101 (see FIG. 7), and the pressure in the cuff 109 (air pressure) is increased.

The diaphragm 120 is fixed to the first valve housing 191 and the second valve housing 192 such that the surrounding area of the hole portion 121 in the diaphragm 120 is in contact with the valve seat 138. The valve seat 138 presses the surrounding area of the hole portion 121 in the diaphragm 120.

In this way, the air flowing out of the hole portion 121 through the first vent 111 in the valve 101 flows from the hole portion 121 into the first upper valve room 133 and the second upper valve room 134 with a pressure slightly lower than the discharge pressure of the piezoelectric pump 10. The discharge pressure of the piezoelectric pump 10 is applied to the second lower valve room 132.

Therefore, in the valve 101, the pressure in the second lower valve room 132 is slightly higher than that in the second upper valve room 134, and the state in which the diaphragm 120 seals the third vent 113 and opens the hole portion 121 is maintained.

As illustrated in FIGS. 3 and 4, because each of the valve rooms 131, 132, 133, and 134 in the valve 101 has a circular outer shape, tension is evenly applied to the diaphragm 120 (in particular, adjacent region of the surrounding area of the hole portion 121).

Thus, the occurrence of states where the hole portion 121 in the diaphragm 120 is inclined with respect to the valve seat 138 when the diaphragm 120 comes into contact therewith and the occurrence of states where the hole portion 121 in the diaphragm 120 is displaced in a horizontal direction with respect to the valve seat 138 can be suppressed. Consequently, according to the valve 101, each of the valve elements can be smoothly opened and closed.

Figure 8:
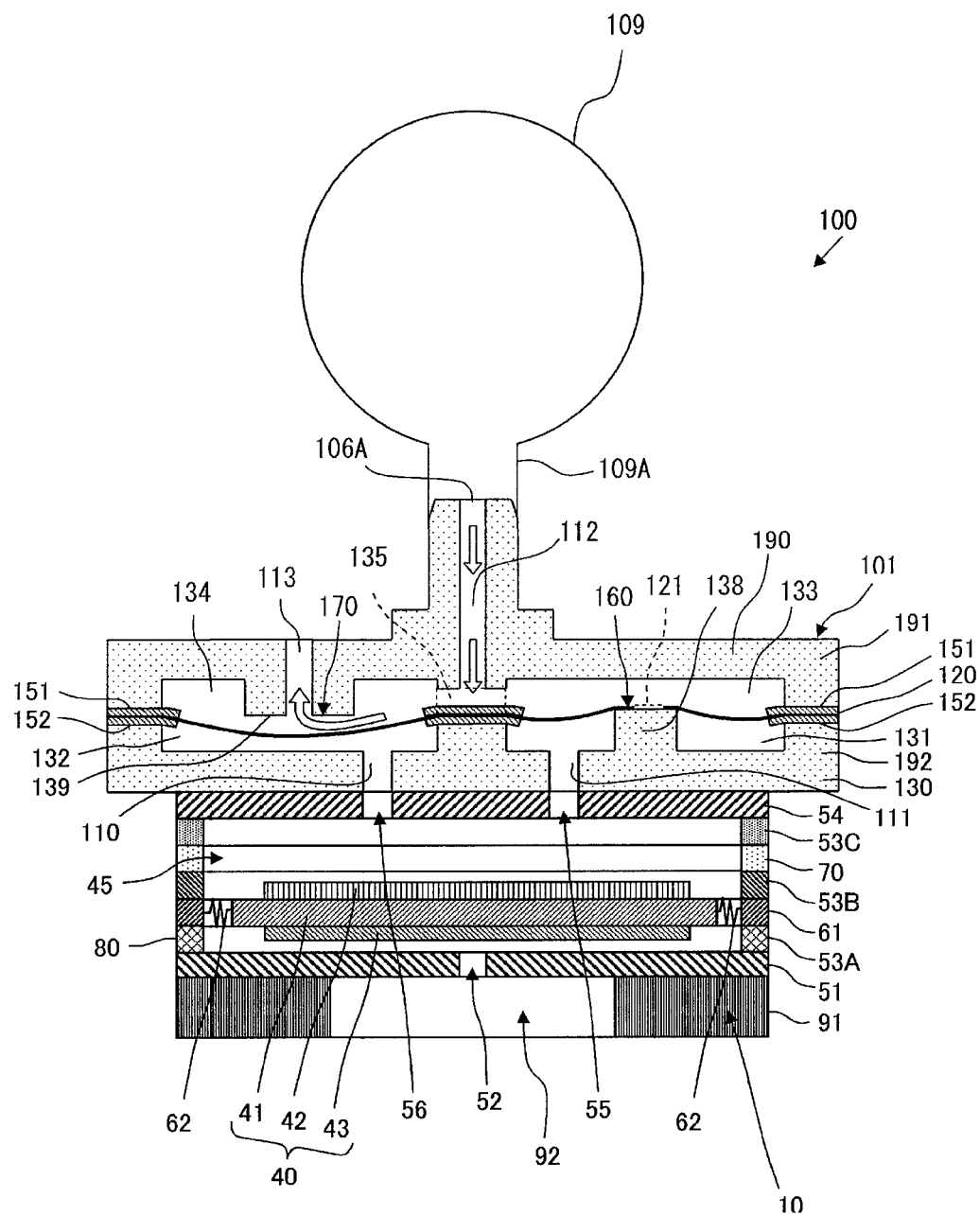
FIG. 8 is an illustration for describing air streams in the fluid control apparatus 100 immediately after the piezoelectric pump 10 illustrated in FIG. 1 stops being driven.

FIG. 8 is an illustration for describing air streams in the fluid control apparatus 100 immediately after the piezoelectric pump 10 illustrated in FIG. 1 stops being driven.

When measurement of the blood pressure is completed, the fluid control apparatus 100 stops driving the piezoelectric pump 10. When the piezoelectric pump 10 stops being driven, air in the pump room 45, first lower valve room 131, and second lower valve room 132 is quickly ejected from the suction hole 52 and cavity 92 to the outside of the fluid control apparatus 100. The pressure in the cuff 109 is applied to the first upper valve room 133 and the second upper valve room 134 through the second vent 112.

Therefore, in the check valve 160, the pressure in the first lower valve room 131 becomes lower than the pressure in the first upper valve room 133. The diaphragm 120 comes into contact with the valve seat 138 and seals the hole portion 121.

In the exhaust valve 170, the pressure in the second lower valve room 132 becomes lower than the pressure in the second upper valve room 134. The diaphragm 120 becomes separated from the valve seat 139 and opens the third vent 113.

That is, in the valve 101, the second vent 112 and the third vent 113 communicate with each other through the communication path 135 and the second upper valve room 134. Thus, air in the cuff 109 is quickly ejected from the third vent 113 through the second vent 112, communication path 135, and second upper valve room 134 (see FIG. 8).

Consequently, according to the valve 101 in the present embodiment, after compressed air is charged into the cuff 109, the air can be quickly ejected from the cuff 109.

As previously described, in the valve 101, part of the second seal member 152 is located inside the first lower valve room 131 and the second lower valve room 132, and part of the first seal member 151 is located inside the first upper valve room 133 and the second upper valve room 134.

Thus, the first seal member 151 and the second seal member 152 can bond the first valve housing 191, the second valve housing 192, and the diaphragm 120 and can capture foreign matter present inside each of the valve rooms 131, 132, 133, and 134.

Consequently, according to the valve 101, if foreign matter enters the valve 101, for example, malfunction caused by the foreign matter can be suppressed. In particular, in the exhaust valve 170, blockage of the third vent 113 in the valve seat 139 by the foreign matter can be suppressed.

The fluid control apparatus 100 including the valve 101 in the present embodiment can achieve substantially the same advantages.

The performance of the valve 101 can be expressed by a pressure loss and a leak pressure. In particular, air leakage from the first vents 110 and 111 to the third vent 113 in the valve 101 while the piezoelectric pump 10 is driven materially affects the performance of the valve 101.

The pressure loss is a loss occurring when the check valve 160 is brought into an open state. Tension is applied to the diaphragm 120, and the valve seat 138 is disposed in the second valve housing 192 so as to press the surrounding area of the hole portion 121 in the diaphragm 120. That is, a stress from the first upper valve room 133 toward the first lower valve room 131 is applied to the diaphragm 120.

Thus, when the check valve 160 is brought into an open state, a pressure P2 in the first upper valve room 133 becomes lower than a pressure P1 in the first lower valve room 131 by the amount corresponding to the above-described stress. The pressure loss can be calculated from the expression "pressure loss=pressure P1 in first lower valve room 131—pressure P2 in first upper valve room 133."

Due to this pressure loss, a force for bringing the exhaust valve 170 into a closed state (force that presses the diaphragm 120 to the valve seat 139 from the side of the second lower valve room 132) is continuously applied to the exhaust valve 170 while air is sent from the first vent 111 in the valve 101 to the cuff 109. Thus, the exhaust valve 170 is brought into the closed state.

If the pressure loss is small, the difference between the pressure P2 in the first upper valve room 133 and the pressure P1 in the first lower valve room 131 is small. That is, the force for bringing the exhaust valve 170 into the closed state (force that presses the diaphragm 120 to the valve seat 139 from the side of the second lower valve room 132) reduces, and air leakage from the first vents 110 and 111 to the third vent 113 in the valve 101 increases.

If the leakage is large, efficiency in charging air from the first vent 111 in the valve 101 into the cuff 109 deceases. The valve 101 suppresses leakage of air from the cuff 109 through the third vent 113 by using the pressure loss caused by the tension of the diaphragm 120.

The leak pressure can be calculated from the expression "leak pressure=pressure in cuff 109 while piezoelectric pump 10 is driven—pressure in cuff 109 five seconds after piezoelectric pump 10 stops being driven."

Figure 12:
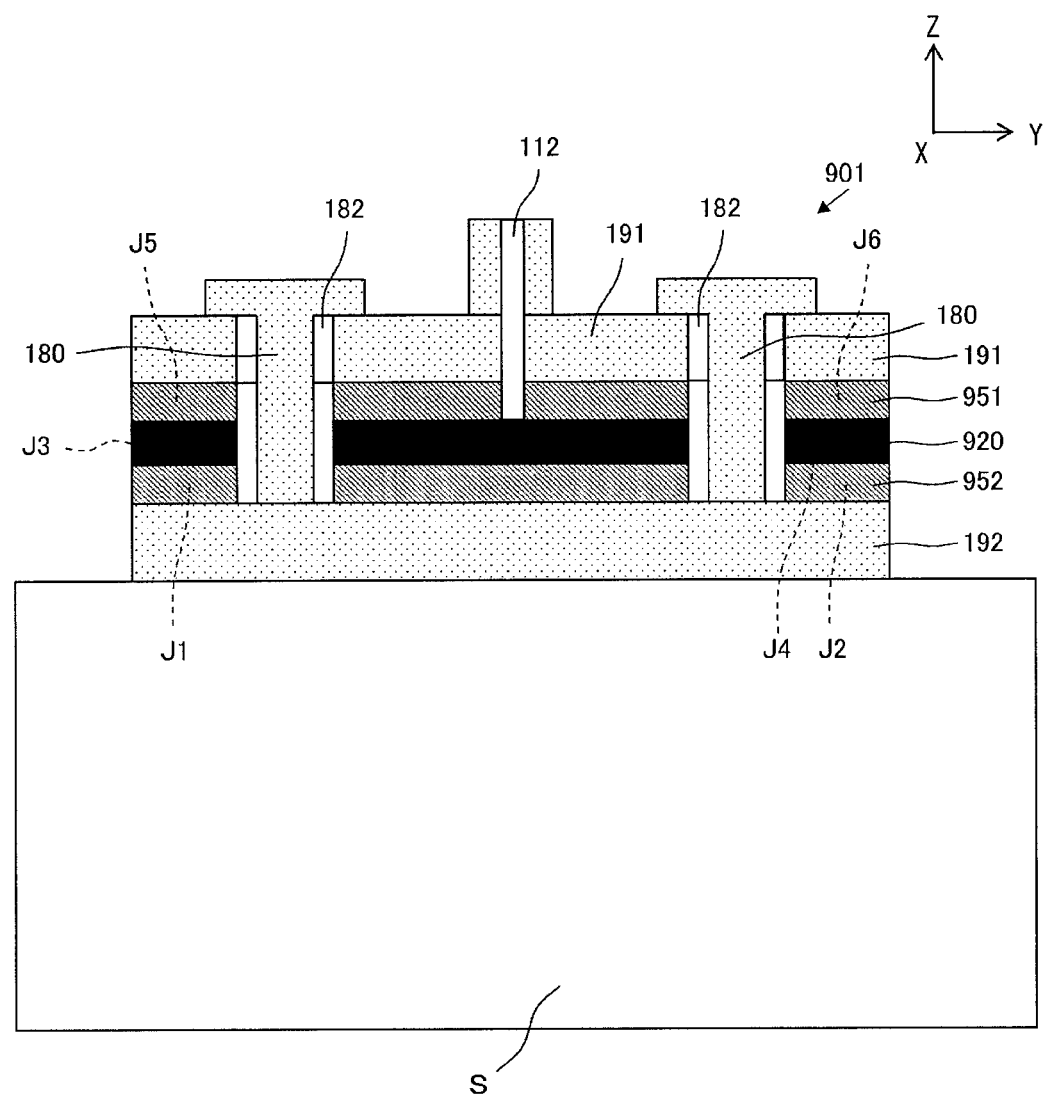
FIG. 12 is a cross-sectional view of a main portion of the valve 901 illustrated in FIG. 10.
Figure 13:
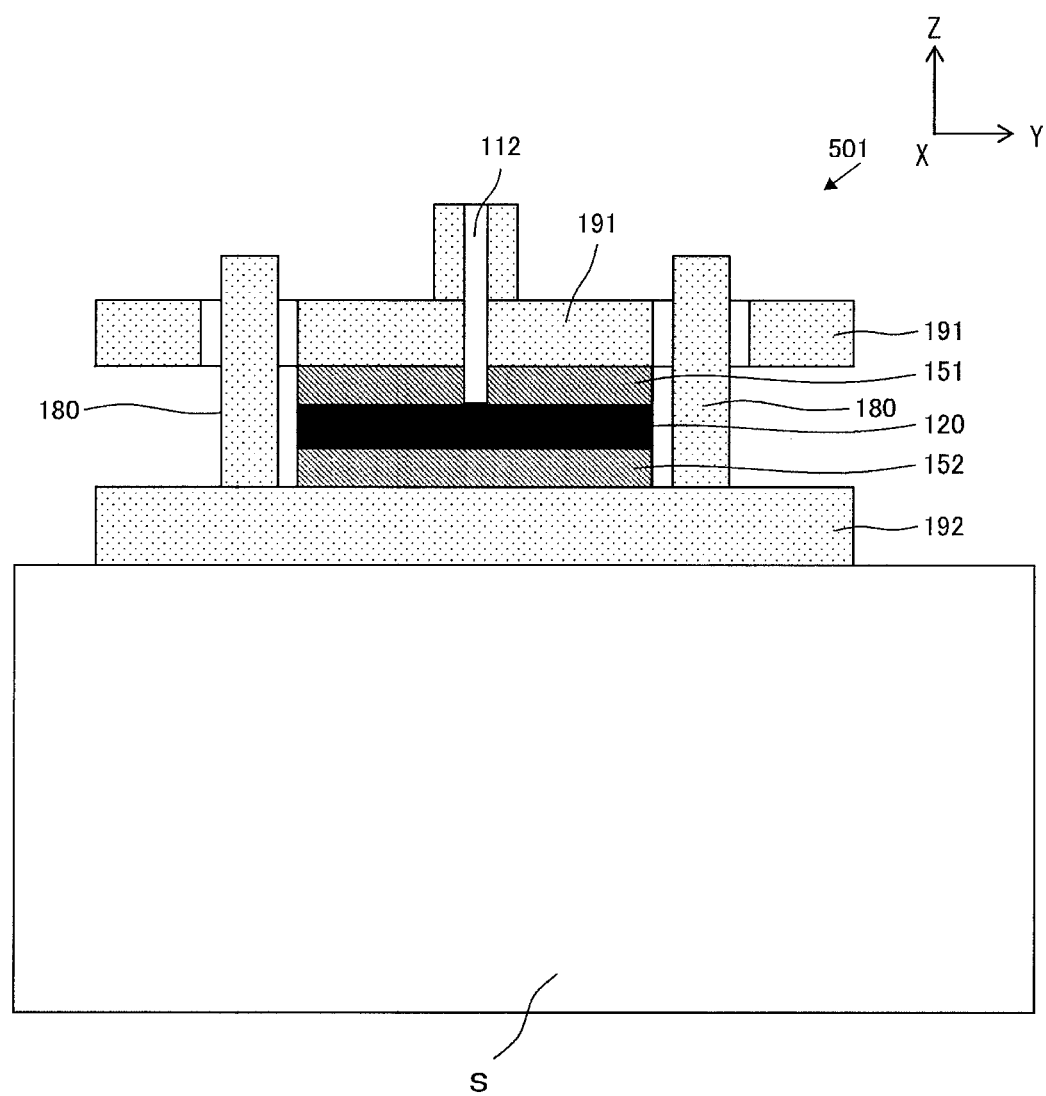
FIG. 13 is a cross-sectional view of a main portion of the valve 501 before the valve 501 is heat-staked according to the second comparative example.

Comparison among the valve 101 (see FIG. 1) according to the embodiment of the present disclosure, the valve 901 (see FIG. 12) according to the first comparative example, and the valve 501 (see FIG. 13) according to the second comparative example is described below.

As previously explained, the valve 501 differs from the valve 901 in that it includes the first seal member 151, second seal member 152, and diaphragm 120, in which the outer side portions J1 to J6 (see FIGS. 12 and 13) nearer the outer edges than the check valve 160 and the exhaust valve 170, as seen in the x-axis direction in plan view, are removed from the first seal member 951, diaphragm 920, and second seal member 952. The valve 101 differs from the valve 501 in that it includes the second protrusions 181.

Figure 9:
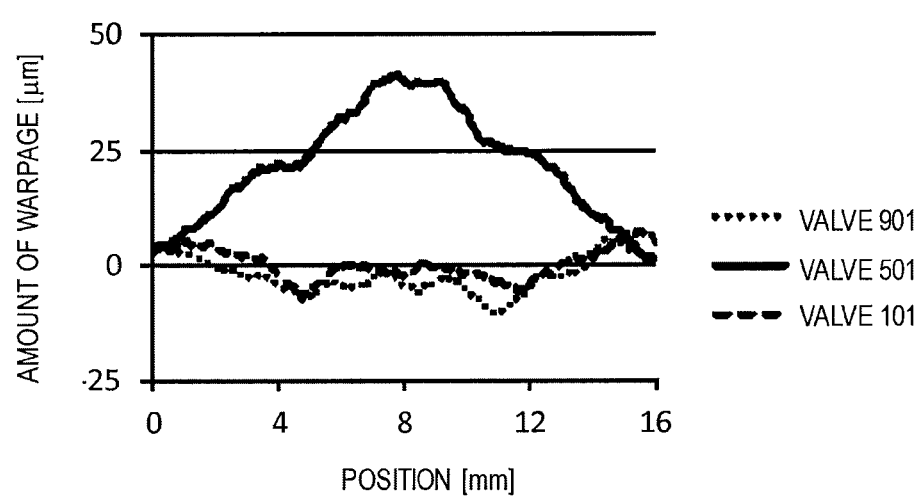
FIG. 9 illustrates a relationship between the position in a second valve housing 192 and the amount of warpage of the second valve housing 192 in the valve 101 according to the embodiment of the present disclosure, in a valve 901 according to a first comparative example, and in a valve 501 according to a second comparative example.
Figure 10:
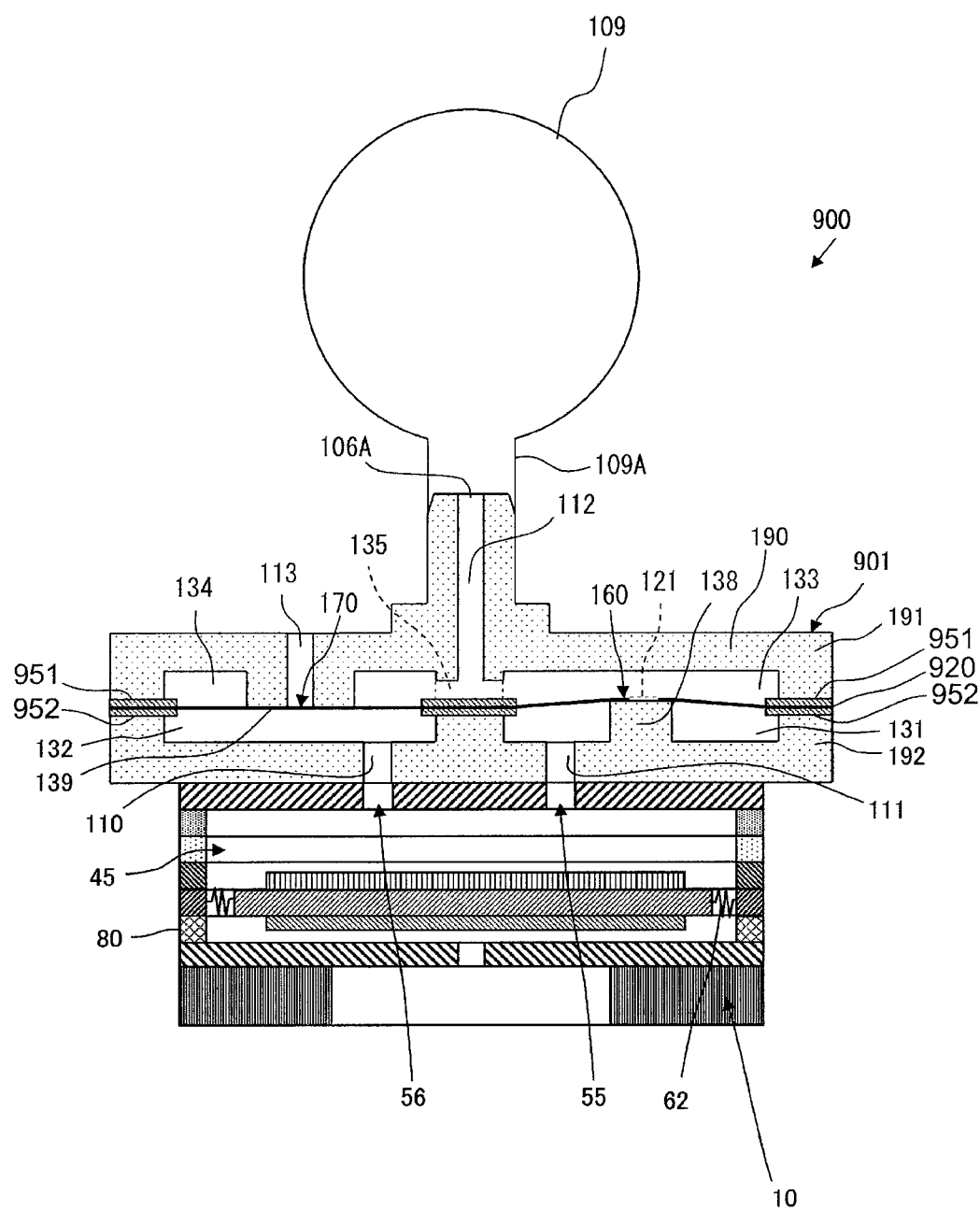
FIG. 10 is a cross-sectional view of a main portion of a fluid control apparatus 900 according to the first comparative example.
Figure 11:
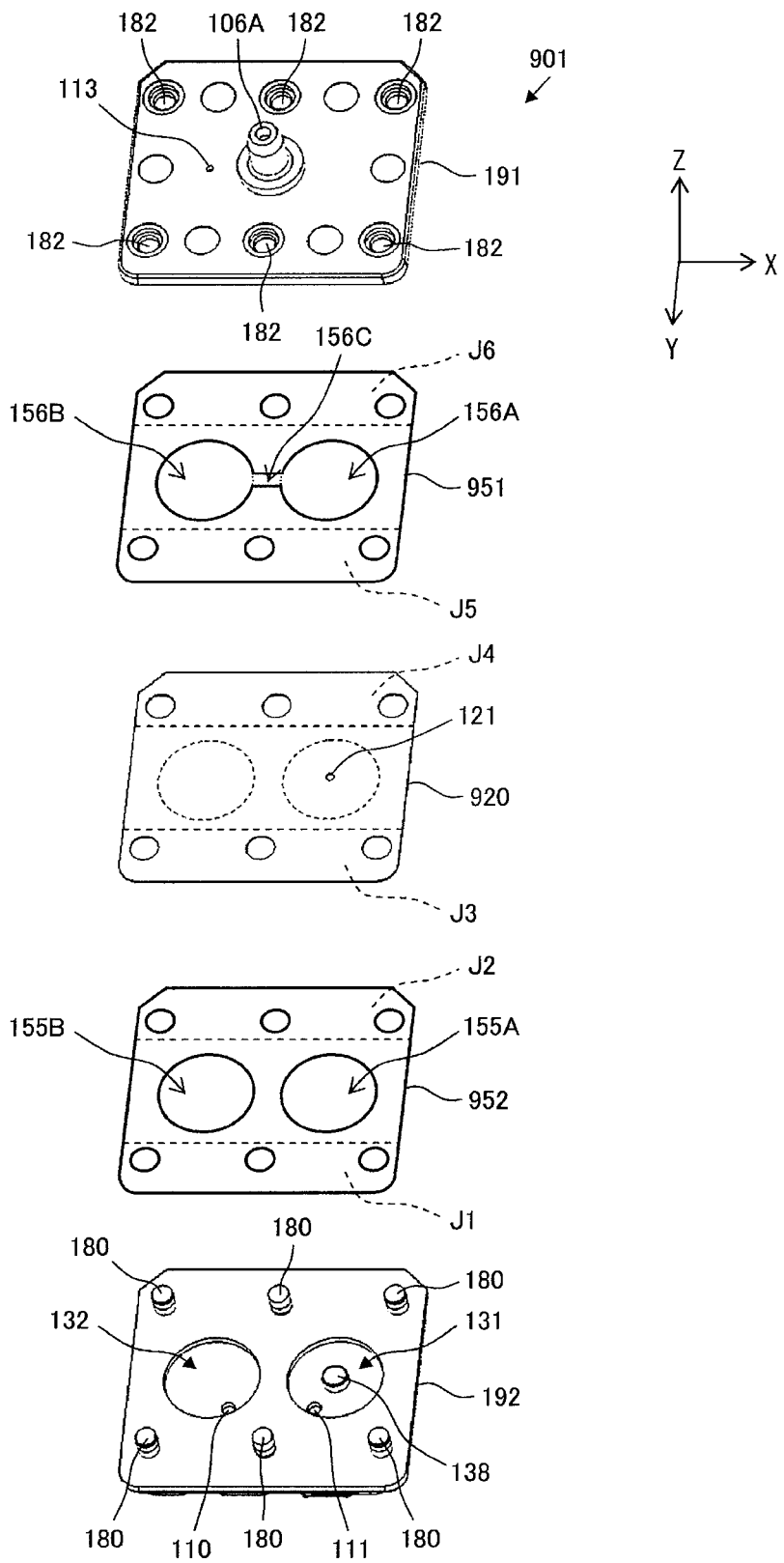
FIG. 11 is an exploded perspective view of the valve 901 illustrated in FIG. 10.

FIG. 9 illustrates a relationship between the position in the second valve housing 192 and the amount of warpage of the second valve housing 192 in the valve 101 according to the embodiment of the present disclosure, in the valve 901 according to the first comparative example, and in the valve 501 according to the second comparative example. FIG. 9 illustrates results of measurement of the amount of warpage from point A through point B to point C in the second valve housing 192 in valve 101, valve 901, and valve 501 by using a laser displacement gage.

As illustrated in FIG. 5, the points A and C are located in an outer side portion with respect to the first protrusions 180 in the second valve housing 192, and the point B is located in an inner side portion with respect to the first protrusions 180 in the second valve housing 192.

Next, results of measurement by driving the piezoelectric pump 10 and applying discharge pressure 40 kPa of the piezoelectric pump 10 to the valves 101, 501, and 901, and measuring a pressure loss and leak pressure in the valves 101, 501, and 901 are listed in Table 1.

TABLE 1

|  | Pressure Loss [kPa] | Leak Pressure [kPa] |
| --- | --- | --- |
| Valve 101 | 0.7 | 0.1 |
| Valve 501 | 0.1 | 1.1 |
| Valve 901 | 0.7 | 0.1 |

The experiment reveals that the pressure loss in the valve 501 is 0.1 kPa and the pressure loss in each of the valves 101 and 901 is 0.7 kPa and that the leak pressure in the valve 501 is 1.1 kPa and the leak pressure in each of the valves 101 and 901 is 0.1 kPa.

Possible reasons for the above results are described below. For the valve 501, when the multilayer body consisting of the first valve housing 191, first seal member 151, diaphragm 120, second seal member 152, and second valve housing 192 is placed on the stage S and the end portions of the six first protrusions 180 are heat-staked, the outer side portion with respect to the first protrusions 180 in the first valve housing 191 is warped toward the second valve housing 192. Thus, for the valve 501, sufficient tension of the diaphragm 120 is not obtainable, that is, a pressure loss equivalent to that in the valve 901 does not occur, and the leak pressure is higher than that in the valves 101 and 901.

In contrast, for the valve 101, when the multilayer body is placed on the stage S and the end portions of the six first protrusions 180 are heat-staked, the outer side portion with respect to the first protrusions 180 in the first valve housing 191 comes into contact with the six second protrusions 181 and warpage can be suppressed. Thus, for the valve 101, sufficient tension of the diaphragm 120 is obtainable, that is, a pressure loss equivalent to that in the valve 901 occurs, and air leakage from the inside of the valve 101 can be suppressed.

Consequently, according to the valve 101 in the present embodiment, the manufacturing cost of the valve 101 can be reduced without necessarily decreasing the performance of the valve, as compared with traditional valves.

Other Embodiments

In the foregoing embodiment, air is used as the fluid. Other forms can also be used. Gas other than air can also be used as the fluid.

The pump in the foregoing embodiment includes the piezoelectric actuator 40, which bends and vibrates in a unimorph manner. The pump may also include an actuator that includes piezoelectric elements attached to both surfaces of a vibrating plate and bends and vibrates in a bimorph manner.

The pump in the foregoing embodiment includes the piezoelectric actuator 40, which bends and vibrates due to expansion and contraction of the piezoelectric element 42. Other forms may also be used. For example, the pump may include an actuator that bends and vibrates by electromagnetic driving.

In the foregoing embodiment, the piezoelectric element is made of a PZT-based ceramic material. Other forms may also be used. For example, the piezoelectric element may be made of a lead-free piezoelectric ceramic material, such as a potassium sodium niobate-based ceramic material and an alkali niobate-based ceramic material.

In the foregoing embodiment, the second protrusions 181 are disposed in the second valve housing 192. Other forms may also be used. The second protrusions 181 may be disposed in the first valve housing 191.

The valve 101 in the foregoing embodiment includes the second seal member 152, in which the circumference of the first through hole 155A is smaller than that of the first lower valve room 131 and the circumference of the first through hole 155B is smaller than that of the second lower valve room 132 (see FIG. 1). Other forms may also be used. For example, the valve 101 may include a second seal member in which the circumference of the first through hole 155A is the same as that of the first lower valve room 131 and the circumference of the first through hole 155B is the same as that of the second lower valve room 132.

Similarly, the valve 101 in the foregoing embodiment includes the first seal member 151, in which the circumference of the second through hole 156A is smaller than that of the first upper valve room 133 and the circumference of the second through hole 156B is smaller than that of the second upper valve room 134 (see FIG. 1). Other forms may also be used. For example, the valve 101 may include a first seal member in which the circumference of the second through hole 156A is the same as that of the first upper valve room 133 and the circumference of the second through hole 156B is the same as that of the second upper valve room 134.

Lastly, the description of the above embodiments is to be considered in all respects only as illustrative and not restrictive. The scope of the disclosure is indicated by the appended claims rather than by the foregoing embodiment. All changes that come within the meaning and range of equivalency of the claims are to be embraced within their scope.

REFERENCE SIGNS LIST

S stage
10 piezoelectric pump
40 piezoelectric actuator
41 vibrating plate
43 strengthening plate
45 pump room
51 flexible plate
52 suction hole
53A, 53B, 53C spacer
54 lid plate
55, 56 discharge hole
57 fixed portion
58 movable portion
60 vibrating plate unit
61 frame plate
62 coupling portion
63, 72 external terminal
70 electrode conduction plate
71 frame member
73 internal terminal
80 pump housing
91 base
92 cavity
100 fluid control apparatus
101 valve
106A cuff connection port
109 cuff
109A arm band rubber tube
110, 111 first vent
112 second vent
113 third vent
120 diaphragm
121 hole portion
131 first lower valve room
132 second lower valve room
133 first upper valve room
134 second upper valve room
135 communication path
138, 139 valve seat
140 actuator
151 first seal member
152 second seal member
155A, 155B first through hole
156A, 156B second through hole
160 check valve
170 exhaust valve
180 first protrusion
181 second protrusion
182 cavity
191 first valve housing
192 second valve housing
501 valve
900 fluid control apparatus
901 valve
920 diaphragm
951 first seal member
952 second seal member

The invention claimed is:

1. A fluid control apparatus comprising:
a pump having a discharge hole; and
a valve comprising:
   a diaphragm having a hole portion;
   a first seal member disposed on a first principal surface of the diaphragm;
   a first valve housing joined to the diaphragm with the first seal member disposed therebetween, the first valve housing having a first hole and a first valve room located near the first principal surface of the diaphragm and communicating with the first hole;
   a second seal member disposed on a second principal surface of the diaphragm; and
   a second valve housing joined to the diaphragm with the second seal member disposed therebetween, the second valve housing having a second hole and a second valve room located near the second principal surface of the diaphragm and communicating with the second hole,
   wherein a surrounding area of the hole portion in the diaphragm directly contacts the second valve housing, and the hole portion is covered therewith,
   wherein the second valve room comprises a valve seat which abuts the surrounding area of the hole portion in the diaphragm, wherein the surrounding area of the hole portion in the diaphragm is a portion of the second principal surface of the diaphragm, and wherein the valve seat is coaxial with the hole portion,
   wherein the first hole in the first valve housing is connected to a fluid storage portion that stores fluid,
   wherein the second hole in the second valve housing is connected to the discharge hole in the pump,
   wherein the first valve housing has a third hole, and wherein the first principal surface of the diaphragm is configured to contact the first valve housing and cover the third hole.

2. The fluid control apparatus according to claim 1, wherein each of the first seal member, the diaphragm, and the second seal member has a perimeter smaller than a perimeter of each of the first valve housing and the second valve housing.

3. The fluid control apparatus according to claim 1, wherein the second valve housing includes a plurality of first protrusions located on an outer side portion with respect to the second valve room.

4. The fluid control apparatus according to claim 3, wherein at least one of the first valve housing and the second valve housing includes a plurality of second protrusions located on an outer side portion with respect to the plurality of first protrusions.

5. The fluid control apparatus according to claim 4, wherein the height of each of the plurality of second protrusions is equal to or greater than a sum of a thickness of the first seal member and a thickness of the second seal member.

6. The fluid control apparatus according to claim 1, wherein the first valve housing includes a plurality of cavities located in an outer side portion with respect to the first valve room, the second valve housing includes a plurality of protrusions located on an outer side portion with respect to the second valve room, the diaphragm is held between the first valve housing and the second valve housing with the first seal member and the second seal member disposed therebetween by fitting the plurality of protrusions into the plurality of cavities.

7. The fluid control apparatus according to claim 4, wherein each of the plurality of second protrusions has a height smaller than a height of each of the plurality of first protrusions.

8. The fluid control apparatus according to claim 1, wherein the first seal member has through holes, each having a diameter that is smaller than or equal to a width of the first valve housing.

9. The fluid control apparatus according to claim 1, wherein the second seal member has through holes, each having a diameter that is smaller than or equal to a width of the second valve housing.

10. The fluid control apparatus according to claim 1, wherein the fluid is air.

11. An apparatus for measuring blood pressure of a subject including:

the fluid control apparatus according to claim 1.

12. The fluid control apparatus according to claim 4, wherein the height of each of the plurality of second protrusions is equal to a sum of a thickness of the first seal member, a thickness of the second seal member, and a thickness of the diaphragm.

13. A fluid control apparatus comprising:
a pump having a discharge hole; and
a valve comprising:
   a diaphragm having a hole portion;
   a first seal member disposed on a first principal surface of the diaphragm;
   a first valve housing joined to the diaphragm with the first seal member disposed therebetween, the first valve housing having a first hole and a first valve room located near the first principal surface of the diaphragm and communicating with the first hole;
   a second seal member disposed on a second principal surface of the diaphragm; and
   a second valve housing joined to the diaphragm with the second seal member disposed therebetween, the second valve housing having a second hole and a second valve room located near the second principal surface of the diaphragm and communicating with the second hole,
wherein a surrounding area of the hole portion in the diaphragm directly contacts the second valve housing, and the hole portion is covered therewith,
wherein the second valve room comprises a valve seat which abuts the surrounding area of the hole portion in the diaphragm wherein the valve seat comprises a protrusion extending in a direction towards the second principal surface of the diaphragm, and wherein the valve seat is configured to cover the hole portion,
wherein the first hole in the first valve housing is connected to a fluid storage portion that stores fluid,
wherein the second hole in the second valve housing is connected to the discharge hole in the pump,
wherein the first valve housing has a third hole, and wherein the first principal surface of the diaphragm is configured to contact the first valve housing and cover the third hole.

\* \* \* \* \*